United States Patent [19]

Lora et al.

[11] Patent Number: 4,764,596
[45] Date of Patent: Aug. 16, 1988

[54] RECOVERY OF LIGNIN

[75] Inventors: Jairo H. Lora, Media, Pa.; Raphael Katzen, Cincinnati, Ohio; Malcolm Cronlund, Chester Springs; Chih F. Wu, King of Prussia, both of Pa.

[73] Assignee: Repap Technologies Inc., Valley Forge, Pa.

[21] Appl. No.: 940,460

[22] Filed: Dec. 11, 1986

Related U.S. Application Data

[63] Continuation-in-part of Ser. No. 795,069, Nov. 5, 1985, abandoned.

[51] Int. Cl.$^4$ ............................ C07G 1/00; D21C 3/20
[52] U.S. Cl. ..................................... 530/507; 162/16; 162/29; 162/40; 162/77
[58] Field of Search ........................... 530/507; 162/16

[56] References Cited

U.S. PATENT DOCUMENTS

| | | | |
|---|---|---|---|
| 1,856,567 | 5/1932 | Kleinert et al. | 162/17 |
| 2,380,448 | 7/1945 | Katzen | 530/507 |
| 3,585,104 | 6/1971 | Kleinert | 162/17 |
| 4,100,016 | 7/1978 | Diebold et al. | 162/16 |

OTHER PUBLICATIONS

Marchessault et al., "Monomers and Oligomers from Wood", Pulp & Paper Mag. Canada, Transactions 6, 52–56, (1980).
Marchessault et al., "Characterization of Aspen Exploded Wood Lignin", Can. J. Chem. 60, 2372–2382, (1982).
Lora et al., "Organosolv Pulping: A Versatile Approach", TAPPI Proceedings, 1984 Research and Development Conference, pp. 215–221, (1984).
Myerly et al., "The Forest Refinery", Chemtech", 186–192, (1981).
Rydholm, *Pulping Processes*, Interscience Publishers, New York, 1971.
Glasser, "Potential Role of Lignin in Tomorrow's Wood Utilization Technologies", Forest Products J., 31, No. 3, pp. 24–29, (1981).

*Primary Examiner*—Earl Nielsen
*Attorney, Agent, or Firm*—Dilworth, Paxson, Kalish & Kauffman

[57] ABSTRACT

Lignin is precipitated in high yields and at high rates from a black liquor produced by pulping wood at high temperatures and pressures with an aqueous lower aliphatic alcohol solvent. The lignin is precipitated by diluting the black liquor with water and an acid to form a solution with a pH of less than about 3, an alcohol content of less than about 30% by volume and a temperature of less than about 75° C. The precipitated lignin, when subsequently dried, is in the form of a powder which requires little or no crushing to convert it into a fine uniform size suitable for use without further significant processing.

61 Claims, 1 Drawing Sheet

RECOVERY OF LIGNIN

CROSS-REFERENCE TO RELATED APPLICATION

This is a continuation-in-part of application Ser. No. 795,069, filed Nov. 5, 1985, entitled "PROCESS FOR LIGNIN RECOVERY", now abandoned.

BACKGROUND OF THE INVENTION

This invention relates to a process for recovering lignin from a solution of lignin in a water miscible organic solvent such as a lower aliphatic alcohol. This invention particularly relates to a process for recovering lignin from the alcohol/water extract or "black liquor" produced as a by-product of the pulping of wood or other fibrous plant material with an alcohol and water solvent at elevated temperatures and pressures to produce a cellulose pulp. This invention also relates to a lignin product produced by the process.

Processes for treating wood with organic solvents, such as alcohols, to separate the wood's lignin, hemicellulose, sugar and cellulose fractions are now well known. See, for example, Kleinert et al U.S. Pat. No. 1,856,567 and Kleinert U.S. Pat. No. 3,585,104. Such solvent pulping processes have appeared to be attractive alternatives to conventional chemical pulping processes, such as kraft and sulfite pulping processes, which suffer from relatively high equipment costs and pollution problems.

One solvent pulping process, disclosed in Diebold et al U.S. Pat. No. 4,100,016, has appeared to be particularly attractive in providing highly efficient recovery of its alcohol solvent, separation of the cellulose and lignin fractions of wood, and recovery of cellulose pulp with no appreciable air or water pollution or solid waste products. This patented process has also provided hardwood pulps with yields, strengths, Kappa numbers, viscosities, fiber strengths and bleachability characteristics that are equal to or better than kraft and sulfite hardwood pulps.

However, the recovery of lignin from the alcohol/water black liquor, generated by the solvent pulping process of Diebold et al U.S. Pat. No. 4,100,016, has been relatively inefficient and difficult to control. Lignin has been recovered from the black liquor in this patent by first stripping (preferably vacuum stripping) alcohol from the black liquor and then separating the lignin which precipitates from the stripper bottoms or tails (preferably by thickening and then centrifuging the settled solids from the stripper bottoms). However, a portion of the lignin has tended to precipitate as a sticky tar or gum on the internal surfaces of the stripper, thereby fouling the stripper and reducing its efficiency in recovering alcohol from the black liquor. The lignin also has tended to precipitate from the stripper bottoms as a sticky amorphous mass which has been difficult to handle and has required substantial crushing to convert the lignin mass into a powder.

As a result, more efficient ways have been sought for removing lignin from the black liquor produced by a solvent pulping process such as is disclosed in Diebold et al U.S. Pat. No. 4,100,016. One method has involved precipitating lignin from the alcohol/water black liquor by diluting it with water. See Rydholm, "Pulping Processes", pp. 672–673, Interscience Publishers, New York (1971). However, this method has resulted in very slow settling rates of the lignin, and in some cases, a very stable colloidal suspension of the lignin has been formed which has been difficult to filter or centrifuge. There has been a continuing need, therefore, for a relatively simple way of recovering lignin from an alcohol/water black liquor in high yields and at high rates in an easy to handle and useful form.

SUMMARY OF THE INVENTION

In accordance with this invention, lignin is precipitated in high yields and at high rates from a solution of lignin in a water miscible organic solvent by a process of diluting the lignin-containing solution with water and an acid to form a diluted aqueous solution with: a pH of less than about 3, an organic solvent content of less than about 30% (by volume), and a temperature of less than about 75° C. The precipitated lignin, when subsequently dried, is in the form of a powder which requires little or no crushing to convert it into a fine uniform size suitable for use without further significant processing.

In accordance with another aspect of this invention, a novel lignin is precipitated by the process of this invention. A preferred lignin is characterized by: a number average molecular weight of about 800 to 1500 g/mol; a polydispersity of less than about 4; and a methoxyl content approximately equal to that of native lignin.

DETAILED DESCRIPTION OF THE PREFERRED EMBODIMENT

Figure 1:
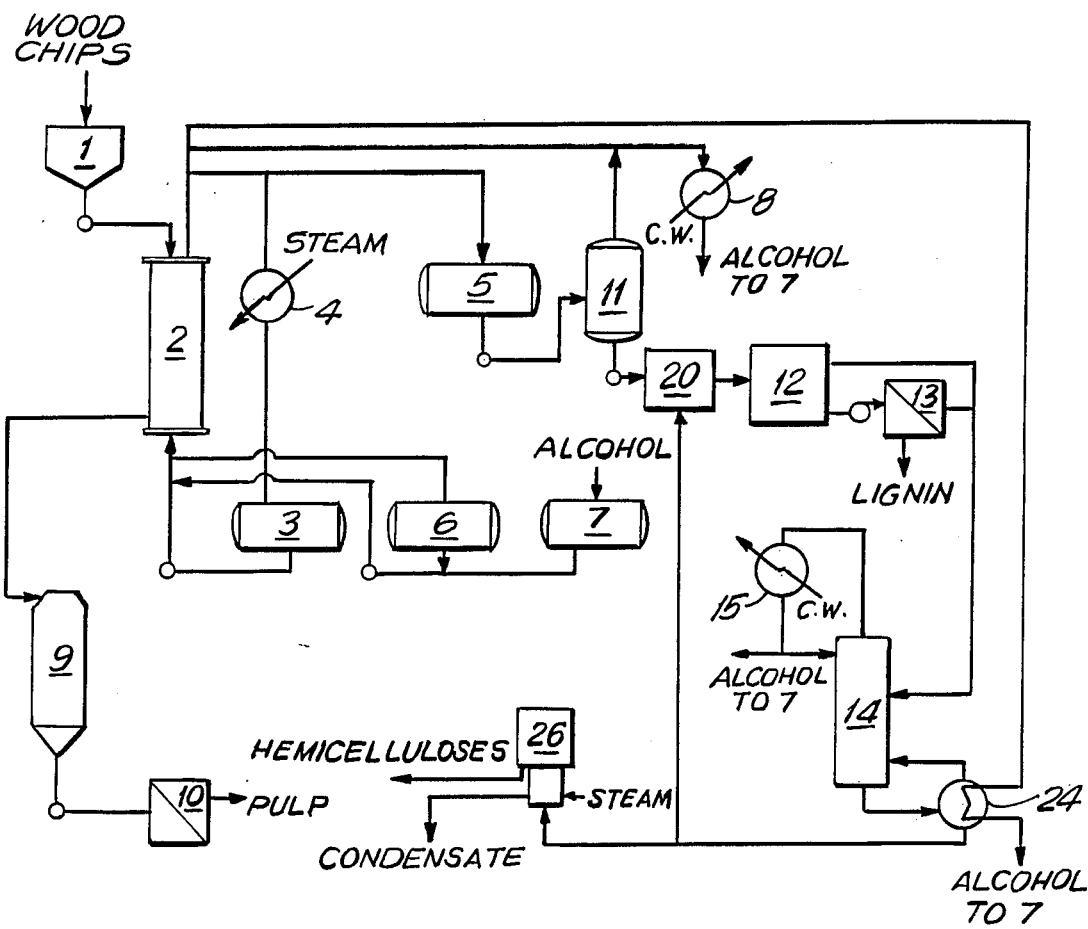
FIG. 1 is a flow chart of a process for producing cellulose pulp from wood by treating the wood with an aqueous alcohol solvent and for recovering lignin from the alcohol/water black liquor that is a by-product of the process.

The process shown in FIG. 1 initially involves pulping a batch of wood chips that are loaded from a hopper 1 into an extractor 2. The extractor 2 is operated in accordance with Diebold et al U.S. Pat. No. 4,100,016 at an elevated temperature (e.g., about 180° to 210° C.) and an elevated pressure (e.g., about 20 to 35 atmospheres) and with a solvent comprising: about 40 to 80% (by volume) of a water miscible lower aliphatic alcohol of 1 to 4 carbon atoms (e.g., methanol, ethanol, isopropanol or tert-butanol); 20 to 60% water; and if needed, a small amount of a strong water soluble acid, such as a mineral acid (e.g., hydrochloric, sulfuric, phosphoric or nitric acid) or an organic acid (e.g., oxalic acid).

Preferably, the wood chips in the extractor 2 are preheated with low pressure steam, and then, a twice-used 60% ethanol/40% water, primary solvent from a primary solvent accumulator 3 contacts the wood chips in the extractor 2. The primary solvent is rapidly recirculated through the extractor 2 and through a peak load (e.g., steam-heated) heat exchanger 4 to raise the temperature of the wood chips to about 190° to 200° C. in a few (preferably not more than about 5) minutes. After this first pulping step is completed, the resulting extract or "black liquor" in the extractor 2 is displaced into a recovery feed accumulator 5 by a once-used 60% ethanol/40% water, secondary solvent (preferably heated to 190° to 200° C.) from a secondary solvent accumulator 6. At the end of this displacement, the secondary solvent in the extractor 2 is displaced into the primary solvent accumulator 3 by a fresh 60% ethanol/40% water solvent (preferably heated to 190° to 200° C.) from a fresh solvent accumulator 7. The fresh solvent in the extractor 2 is then drained into the secondary solvent accumulator 6. Once the extractor 2 has been drained, it is vented, alcohol-rich vapors from the extractor are condensed in a water-cooled ("C. W.") condenser 8, and the resulting ethanol/water mixture from the condenser 8 is recycled to the fresh solvent accumulator 7. After venting the extractor 2, residual alcohol in the pulp in the extractor is then stripped with low pressure steam, and the resulting alcohol/water vapors are condensed and recovered as discussed below. After steam stripping, the pulp in the extractor 2 is sluiced with water, piped to a holding tank 9 and pumped through a pulp screen 10. The pulp can then be suitably subjected to conventional pulp handling, bleaching and paper-making procedures. The extractor 2 can be loaded with another batch of wood chips from the hopper 1, and the wood chips can be contacted by the primary, secondary and fresh solvents from accumulators 3, 6 and 7 as described above.

The lignin, hemicelluloses, other saccharides and extractives (e.g., resins, organic acids, phenols and tannins) from the wood and the ethanol, which are all present in the black liquor at a temperature of about 180° to 210° C. and under a pressure of about 20 to 35 atmospheres in the recovery feed accumulator 5, are then recovered by first flashing the black liquor into a flash tank 11 to recover part of the ethanol. The flash tank 11 can be at atmospheric pressure for simplicity of operation or at reduced pressure to further cool the black liquor and enhance the alcohol recovery. The reduction in pressure in the flash tank 11 causes partial vaporization of the ethanol and leaves the residual black liquor in the flash tank with an ethanol content of about 30 to 45%, preferably about 35 to 40%. The residual black liquor is cooled during this step to a temperature of less than about 95° C., preferably down to about 80° to 92° C., but not below about 70° C. to avoid premature precipitation of lignin in the flash tank 11. The ethanol/water vapors obtained are condensed and recycled, along with any make-up ethanol, water and/or acid, to the fresh solvent accumulator 7 for use in treating subsequent batches of wood chips.

In accordance with this invention, lignin is then separated from the residual black liquor discharged from the flash tank 11. This step is carried out by diluting and preferably cooling the residual black liquor, as it leaves the flash tank 11, with water and acid to form a diluted residual black liquor with: (a) an alcohol content of less than about 30% (by volume), preferably about 10 to 25%, particularly about 12 to 21%, with an alcohol content of about 8% being a practical minimum for subsequently recovering the alcohol economically; (b) a temperature of less than about 75° C., preferably less than about 60° C., particularly about 35° to 55° C.; and (c) a pH of less than about 3, preferably less than about 2.5, particularly about 1.5 to 2.5. In this step, particular temperatures are not critical, although providing higher temperatures in the diluted residual black liquor will generally increase settling rates of the lignin but will yield a darker colored lignin and may decrease its yields. About 75° C. is a maximum temperature to avoid the formation of tarry lignin precipitates, and ambient temperature (e.g., about 20° C.) is a practical minimum, although lower temperatures (e.g., down to about 0° C.) can be used if low settling rates can be tolerated. Temperatures below about 65° C., particularly below about 60° C., provide a significantly lighter colored lignin precitate. Also, particular pH's of the diluted residual black liquor are not critical in this step, but lower pH's increase the yield of precipitated lignin from the diluted residual black liquor and permit the use of higher temperatures in the diluted residual black liquor. However, lowering pH below about 1 provides little or no additional improvement in yield, and for this reason, a pH of about 1 is a practical minimum although lower pH's can be used. At a pH of less than about 3, lignin will precipitate from the diluted residual black liquor in high yield and at a high rate as fine solids. These lignin solids can then be separated from the remaining diluted residual black liquor supernatant in a conventional manner. Preferably, the lignin solids are separated by: allowing them to settle out as a paste of about 6 to 12% (by weight) solids in a conventional clarifier or settling tank 12; then concentrating this paste of lignin solids in a conventional centrifugal separator 13 to form a wet cake of about 30 to 40% solids; and then drying this wet cake to form a uniform fine, free flowing powder.

In diluting the residual black liquor from the flash tank 11 with the water and acid to precipitate lignin, any conventional water soluble acid can be utilized which will provide the diluted residual black liquor with a pH of less than about 3.0, preferably less than about 2.50. For example, a strong mineral acid (e.g., hydrochloric, nitric, sulfuric or phosphoric acid) or a strong organic acid (e.g., oxalic acid) can be used. Preferably, the water and acid are mixed together before they are used to dilute the residual black liquor. In this regard, a particularly preferred mixture of acid and water is a residual black liquor supernatant that is derived from a previous batch of wood chips and that has been recycled and used to dilute the residual black liquor from the flash tank 11 after: (a) the supernatant has been separated from the lignin solids from the previous batch of wood chips in the settling tank 12 and the centrifugal separator 13; and (b) the alcohol content of the supernatant has been recovered in a conventional solvent recovery tower 14 provided with a conventional solvent condenser 15 as described below. This recycled residual black liquor supernatant or stripper bottoms, when used for diluting the residual black liquor from the flash tank 11, provides higher yields and faster settling of lignin solids precipitating in the settling tank 12 and centrifugal separator 13.

Figure 2:
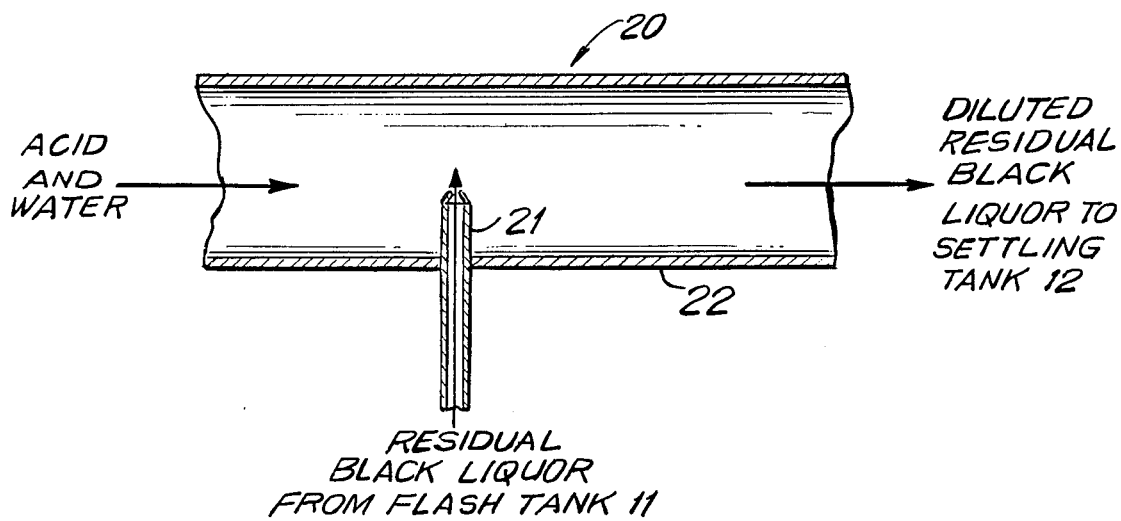
FIG. 2 is a schematic sectional view of an example of an apparatus for precipitating lignin from the alcohol/water black liquor from the process of FIG. 1.

In precipitating lignin from the residual black liquor from the flash tank 11, the method of diluting the residual black liquor with the water and acid also is not critical, so long as there is rapid and intimate mixing of the residual black liquor with the acid and water. For example, the residual black liquor can be suitably diluted by adding it to the acid and water in a conventional static dispersion mixer. The residual black liquor can also be diluted by adding it as a finely divided stream to a stream comprising a solution of the water and acid, for example, by means of a venturi-type device, generally 20, as shown schematically in FIG. 2. The residual black liquor from flash tank 11 in FIG. 1 can be pumped through a small nozzle 21 located at about the center of a pipe 22 in the venturi-type device 20 in FIG. 2, and the acid and water solution can flow in the pipe 22 towards the settling tank 12 in FIG. 1. As the residual black liquor is injected by the nozzle 21 into the acid and water solution in the pipe 22, the residual black liquor is rapidly diluted and cooled by the acid and water in the pipe 22. Lignin rapidly precipitates as fine solids from the resulting diluted residual black liquor in the pipe 22, which solids can be easily collected and concentrated in the settling tank 12 and centrifugal separator 13.

In precipitating lignin in accordance with this invention, the yield and settling rates of the lignin are generally a function of: (a) the wood species; (b) the process conditions utilized in the extractor 2; (c) the temperature, pH and solids content of (i) the residual black liquor from the flash tank 11 and (ii) the acid and water used to dilute it; and (d) the ratio of residual black liquor to the acid and water used to dilute it. For example, the lignin from softwoods, such as spruce, is preferably precipitated at a temperature after dilution of about 40° to 60° C. using an acid and water solution with a pH of about 1.5 to 2.5 and with a ratio of residual black liquor to the acid and water solution of about 0.5 to about 1. For hardwoods such as aspen, it is preferred to use an acid and water solution with a pH of about 1.2 to 2.2 and a temperature after dilution of less than about 50° C. In this regard, it is preferred to use a ratio of residual black liquor to the acid and water solution of: (a) about 0.2 to 0.8 if the temperature after dilution is above about 40° C.; and (b) about 0.6 to 1.0 if the temperature after dilution is less than about 40° C. (e.g., down to ambient temperature). For hardwoods, such as sweetgum, maple and oak, it is preferred to use a temperature after dilution of about 40° to 60° C., an acid and water solution with a pH of about 1.5 to 2.5, and a ratio of residual black liquor to the acid and water solution of about 0.35 to 0.7.

As shown in FIG. 1, the ethanol content of the clarified residual black liquor supernatant from the settling tank 12 and centrifugal separator 13 is preferably recovered in the solvent recovery tower 14 and solvent condenser 15. The ethanol content of the supernatant can be stripped (e.g., down to about 200 ppm) in a conventional manner in the solvent recovery tower 14 at atmospheric pressure. Preferably, the tower 14 is heated by heating and recycling a portion of the bottoms stream from the tower 14 in a heat exchanger 24, using the low pressure steam used to strip residual ethanol from the pulp in the extractor 2. The ethanol/water vapors from the tower 14 are condensed in a conventional manner in the water-cooled condenser 15 (or by heat exchange with the stripper feed) and are then recycled to the fresh solvent accumulator 7 together with the ethanol/water mixture which condenses from the low pressure steam in the heat exchanger 24. In accordance with this invention, the ethanol content of the supernatant from the settling tank 12 and centrifugal separator 13 can be suitably recovered in high yield in a simple manner, without lignin precipitating within the solvent recovery tower 14 and forming tarry or gummy deposits on the internal surfaces of the tower.

A portion of the bottoms stream removed from the solvent recovery tower 14 is preferably concentrated in a conventional manner, for example, in multiple effect evaporators 26. In this step, scaling or fouling of the evaporation equipment is not a significant problem because there are no substantial amounts of high molecular weight lignin in the bottoms stream from the solvent recovery tower 14. The resulting syrup, containing hemicelluloses together with small amounts of other saccharides, extractives and very low molecular weight lignin (i.e., lignin with a molecular weight of less than about 400 g/mol), can be burned to recover its fuel value, used as animal feed, or converted to other chemical products.

A second portion of the bottoms stream removed from the tower 14 is preferably used as the acid and water solution for diluting the residual black liquor from the flash tank 11 in order to precipitate lignin therefrom. In this regard, the second portion of the bottoms stream from the tower 14 is preferably cooled to a temperature of less than about 50° C., preferably about 25° to 40° C. (about 0° C. being a practical minimum), and its pH is adjusted, if necessary, to about 1.0 to 3.0 by adding a strong water soluble acid to it. Then, the cooled and acidified second portion of the bottoms stream (hereinbefore called the "recycled residual black liquor supernatant") is intimately and rapidly mixed (e.g., in the venturi-type device 20 of FIG. 2) with the residual black liquor to dilute and cool the residual black liquor and precipitate lignin.

The very pure lignin, which precipitates as fine solids from the diluted residual black liquor in the settling tank 12, can be subsequently removed from the centrifugal separator 13, water-washed and dried in a conventional manner (e.g., by spin flash drying) to form a fine (e.g., $-80$ mesh) uniform, free flowing, water insoluble powder. This lignin can be characterized as having: a relatively low number average molecular weight of about 800 to 1500 g/mol, preferably about 900 to 1300 g/mol; a narrow molecular weight distribution, i.e., a polydispersity of less than about 4, preferably no more than about 3, particularly only about 1.5 to 2.7; and a methoxyl content approximately equal to the methoxyl content of native lignin (i.e., about 20% for hardwoods and about 14% for softwoods). This lignin also has a glass transition temperature which is preferably about 100° to 170° C., particularly about 130° to 150° C. These characteristics show, inter alia, the purity and low degree of chemical modification of the lignin of this invention. This lignin can be used, for example, as a phenol formaldehyde resin extender in the manufacture of particle board and plywood. This lignin can also be used in the manufacture of molding compounds, urethane and epoxy resins, antioxidants, controlled-release agents and flow control agents.

This invention and many of its attendant advantages will be understood from the foregoing description, and it will be apparent that various modifications and changes can be made in the process for precipitating lignin without departing from the spirit and scope of the invention or sacrificing all of its material advantages, the process hereinbefore described being merely a preferred embodiment. For example, the process of this invention can alternatively be carried out by separately adding an acid and water to a solution of lignin dissolved in a water miscible organic solvent to form a diluted aqueous solution with a pH of less than about 3, an organic solvent content of less than about 30% and a temperature of less than about 75° C., from which diluted solution the lignin will precipitate as uniform fine solids. In this regard, the acid can be separately added to the residual black liquor from the flash tank 11 in FIG. 1 by adding the acid to the primary solvent from the primary solvent accumulator 3 before the primary solvent is used in the extractor 2 for pulping wood chips to produce the black liquor (which becomes, after removal of ethanol in the flash tank 11, the residual black liquor). Also, the process of this invention can be carried out with a water miscible organic solvent other than a lower aliphatic alcohol (preferably ethanol), such as acetone, glycol or glycerol, or with a mixture of such solvents. Also, this process can be carried out with lignin extracted from any fibrous plant material, such as bamboo, bagasse, and cereal straws, and not just wood.

We claim:

1. Process for precipitating lignin from a solution of lignin in a water miscible organic solvent, comprising the step of diluting the lignin-containing solution with water and an acid to form a diluted aqueous solution with: a pH of less than about 3, an organic solvent content of less than about 30% by volume and a temperature of less than about 75° C.

2. The process of claim 1, wherein the organic solvent is a lower aliphatic alcohol of 1 to 4 carbon atoms.

3. The process of claim 2, wherein the diluted aqueous solution has a pH of less than about 2.5.

4. The process of claim 3, wherein the diluted aqueous solution has a temperature of less than about 60° C.

5. The process of claim 4, wherein the diluted aqueous solution has a temperature of about 35° to 55° C.

6. The process of claim 2, wherein the diluted aqueous solution has an alcohol content of about 10 to 25% by volume.

7. The process of claim 6, wherein the diluted aqueous solution has an alcohol content of about 12 to 21% by volume and a temperature of less than about 65° C.

8. The process of claim 6, wherein the diluted aqueous solution has a temperature of less than about 60° C. and a pH of about 1.5 to 2.5.

9. The process of claim 8, wherein the diluted aqueous solution has a temperature of about 35° to 55° C. and an alcohol content of about 12 to 21% by volume.

10. The process of claim 1, wherein the lignin-containing solution contains water before it is diluted with the water and acid.

11. The process of claim 10, wherein the lignin-containing solution is intimately and rapidly mixed with a mixture of the water and acid to form the diluted aqueous solution.

12. The process of claim 1, wherein the lignin-containing solution is obtained by: contacting wood or other fibrous plant material with the organic solvent at an elevated temperature and an elevated pressure to produce a cellulose pulp and a black liquor containing lignin and the organic solvent; and then separating the pulp from the black liquor.

13. The process of claim 12, wherein the acid and water are in a mixture which also contains hemicelluloses, other saccharides, extractives and lignin with a molecular weight of less than about 400 g/mol.

14. The process of claim 13, wherein the acid and water mixture is a recycled aqueous acid obtained by: diluting the black liquor with the aqueous acid to form a diluted black liquor from which lignin is precipitated, leaving a black liquor supernatant; removing the black liquor precipitate from the black liquor supernatant; removing the organic solvent from the black liquor supernatant to produce a residual black liquor supernatant; and then recycling a portion of the residual black liquor supernatant for use as the aqueous acid in diluting the black liquor.

15. The process of claim 14, wherein the organic solvent is a lower aliphatic alcohol of 1 to 4 carbon atoms.

16. The process of claim 15, wherein the diluted black liquor has a pH of less than about 2.5.

17. The process of claim 16, wherein the diluted black liquor has a temperature of less than about 60° C.

18. The process of claim 15, wherein the diluted black liquor has an alcohol content of about 10 to 25% by volume.

19. The process of claim 18, wherein the diluted black liquor has a pH of about 1.5 to 2.5 and a temperature of less than about 60° C.

20. The process of claim 19, wherein the diluted black liquor has a temperature of about 35° to 55° C. and an alcohol content of about 12 to 21% by volume.

21. The process of claim 14, wherein the black liquor contains water before it is diluted with the recycled aqueous acid.

22. The process of claim 21, wherein the black liquor is intimately and rapidly mixed with the recycled aqueous acid to form the diluted black liquor.

23. The process of claim 15, wherein the black liquor has a temperature of about 70° to 95° C. and the recycled aqueous acid has a temperature of less than about 50° C.

24. The process of claim 23, wherein the black liquor has a temperature of about 80° to 92° C. and the recycled aqueous acid has a temperature of about 25° to 40° C.

25. A lignin precipitated by the process of claim 1.

26. The lignin of claim 25 having: a number average molecular weight of about 800 to 1500 g/mol; and a polydispersity of less than about 4.

27. The lignin of claim 26 having: a number average molecular weight of about 900 to 1300 g/mol; and a polydispersity of no more than about 3.

28. The lignin of claim 27 having: a polydispersity of only about 1.5 to 2.7.

29. The lignin of claim 25 which is a paste, a wet cake or a powder.

30. A lignin precipitated by the process of claim 12.

31. The lignin of claim 30 having: a number average molecular weight of about 800 to 1500 g/mol; and a polydispersity of less than about 4.

32. The lignin of claim 31 having: a number of average molecular weight of about 900 to 1300 g/mol; and a polydispersity of no more than about 3.

33. The lignin of claim 32 having: a polydispersity of only about 1.5 to 2.7.

34. The lignin of claim 30 which is a paste, a wet cake or a powder.

35. A lignin precipitated by the process of claim 13.

36. The lignin of claim 35 having: a number average molecular weight of about 800 to 1500 g/mol; and a polydispersity of less than about 4.

37. The lignin of claim 36 having: a number average molecular weight of about 900 to 1300 g/mol; and a polydispersity of no more than about 3.

38. The lignin of claim 37 having: a polydispersity of only about 1.5 to 2.7.

39. The lignin of claim 35 which is a paste, a wet cake or a powder.

40. A lignin precipitated by the process of claim 14.

41. The lignin of claim 40 having: a number average molecular weight of about 800 to 1500 g/mol; and a polydispersity of less than about 4.

42. The lignin of claim 41 having: a number average molecular weight of about 900 to 1300 g/mol; and a polydispersity of no more than about 3.

43. The lignin of claim 42 having: a polydispersity of only about 1.5 to 2.7.

black liquor is rapidly diluted and cooled by the acid and water in the pipe 22. Lignin rapidly precipitates as fine solids from the resulting diluted residual black liquor in the pipe 22, which solids can be easily collected and concentrated in the settling tank 12 and centrifugal separator 13.

In precipitating lignin in accordance with this invention, the yield and settling rates of the lignin are generally a function of: (a) the wood species; (b) the process conditions utilized in the extractor 2; (c) the temperature, pH and solids content of (i) the residual black liquor from the flash tank 11 and (ii) the acid and water used to dilute it; and (d) the ratio of residual black liquor to the acid and water used to dilute it. For example, the lignin from softwoods, such as spruce, is preferably precipitated at a temperature after dilution of about 40° to 60° C. using an acid and water solution with a pH of about 1.5 to 2.5 and with a ratio of residual black liquor to the acid and water solution of about 0.5 to about 1. For hardwoods such as aspen, it is preferred to use an acid and water solution with a pH of about 1.2 to 2.2 and a temperature after dilution of less than about 50° C. In this regard, it is preferred to use a ratio of residual black liquor to the acid and water solution of: (a) about 0.2 to 0.8 if the temperature after dilution is above about 40° C.; and (b) about 0.6 to 1.0 if the temperature after dilution is less than about 40° C. (e.g., down to ambient temperature). For hardwoods, such as sweetgum, maple and oak, it is preferred to use a temperature after dilution of about 40° to 60° C., an acid and water solution with a pH of about 1.5 to 2.5, and a ratio of residual black liquor to the acid and water solution of about 0.35 to 0.7.

As shown in FIG. 1, the ethanol content of the clarified residual black liquor supernatant from the settling tank 12 and centrifugal separator 13 is preferably recovered in the solvent recovery tower 14 and solvent condenser 15. The ethanol content of the supernatant can be stripped (e.g., down to about 200 ppm) in a conventional manner in the solvent recovery tower 14 at atmospheric pressure. Preferably, the tower 14 is heated by heating and recycling a portion of the bottoms stream from the tower 14 in a heat exchanger 24, using the low pressure steam used to strip residual ethanol from the pulp in the extractor 2. The ethanol/water vapors from the tower 14 are condensed in a conventional manner in the water-cooled condenser 15 (or by heat exchange with the stripper feed) and are then recycled to the fresh solvent accumulator 7 together with the ethanol/water mixture which condenses from the low pressure steam in the heat exchanger 24. In accordance with this invention, the ethanol content of the supernatant from the settling tank 12 and centrifugal separator 13 can be suitably recovered in high yield in a simple manner, without lignin precipitating within the solvent recovery tower 14 and forming tarry or gummy deposits on the internal surfaces of the tower.

A portion of the bottoms stream removed from the solvent recovery tower 14 is preferably concentrated in a conventional manner, for example, in multiple effect evaporators 26. In this step, scaling or fouling of the evaporation equipment is not a significant problem because there are no substantial amounts of high molecular weight lignin in the bottoms stream from the solvent recovery tower 14. The resulting syrup, containing hemicelluloses together with small amounts of other saccharides, extractives and very low molecular weight lignin (i.e., lignin with a molecular weight of less than about 400 g/mol), can be burned to recover its fuel value, used as animal feed, or converted to other chemical products.

A second portion of the bottoms stream removed from the tower 14 is preferably used as the acid and water solution for diluting the residual black liquor from the flash tank 11 in order to precipitate lignin therefrom. In this regard, the second portion of the bottoms stream from the tower 14 is preferably cooled to a temperature of less than about 50° C., preferably about 25° to 40° C. (about 0° C. being a practical minimum), and its pH is adjusted, if necessary, to about 1.0 to 3.0 by adding a strong water soluble acid to it. Then, the cooled and acidified second portion of the bottoms stream (hereinbefore called the "recycled residual black liquor supernatant") is intimately and rapidly mixed (e.g., in the venturi-type device 20 of FIG. 2) with the residual black liquor to dilute and cool the residual black liquor and precipitate lignin.

The very pure lignin, which precipitates as fine solids from the diluted residual black liquor in the settling tank 12, can be subsequently removed from the centrifugal separator 13, water-washed and dried in a conventional manner (e.g., by spin flash drying) to form a fine (e.g., −80 mesh) uniform, free flowing, water insoluble powder. This lignin can be characterized as having: a relatively low number average molecular weight of about 800 to 1500 g/mol, preferably about 900 to 1300 g/mol; a narrow molecular weight distribution, i.e., a polydispersity of less than about 4, preferably no more than about 3, particularly only about 1.5 to 2.7; and a methoxyl content approximately equal to the methoxyl content of native lignin (i.e., about 20% for hardwoods and about 14% for softwoods). This lignin also has a glass transition temperature which is preferably about 100° to 170° C., particularly about 130° to 150° C. These characteristics show, inter alia, the purity and low degree of chemical modification of the lignin of this invention. This lignin can be used, for example, as a phenol formaldehyde resin extender in the manufacture of particle board and plywood. This lignin can also be used in the manufacture of molding compounds, urethane and epoxy resins, antioxidants, controlled-release agents and flow control agents.

This invention and many of its attendant advantages will be understood from the foregoing description, and it will be apparent that various modifications and changes can be made in the process for precipitating lignin without departing from the spirit and scope of the invention or sacrificing all of its material advantages, the process hereinbefore described being merely a preferred embodiment. For example, the process of this invention can alternatively be carried out by separately adding an acid and water to a solution of lignin dissolved in a water miscible organic solvent to form a diluted aqueous solution with a pH of less than about 3, an organic solvent content of less than about 30% and a temperature of less than about 75° C., from which diluted solution the lignin will precipitate as uniform fine solids. In this regard, the acid can be separately added to the residual black liquor from the flash tank 11 in FIG. 1 by adding the acid to the primary solvent from the primary solvent accumulator 3 before the primary solvent is used in the extractor 2 for pulping wood chips to produce the black liquor (which becomes, after removal of ethanol in the flash tank 11, the residual black liquor). Also, the process of this invention can be carried out with a water miscible organic solvent other than a lower aliphatic alcohol (preferably ethanol), such as acetone, glycol or glycerol, or with a mixture of such solvents. Also, this process can be carried out with lignin extracted from any fibrous plant material, such as bamboo, bagasse, and cereal straws, and not just wood.

We claim:

1. Process for precipitating lignin from a solution of lignin in a water miscible organic solvent, comprising the step of diluting the lignin-containing solution with water and an acid to form a diluted aqueous solution with: a pH of less than about 3, an organic solvent content of less than about 30% by volume and a temperature of less than about 75° C.

2. The process of claim 1, wherein the organic solvent is a lower aliphatic alcohol of 1 to 4 carbon atoms.

3. The process of claim 2, wherein the diluted aqueous solution has a pH of less than about 2.5.

4. The process of claim 3, wherein the diluted aqueous solution has a temperature of less than about 60° C.

5. The process of claim 4, wherein the diluted aqueous solution has a temperature of about 35° to 55° C.

6. The process of claim 2, wherein the diluted aqueous solution has an alcohol content of about 10 to 25% by volume.

7. The process of claim 6, wherein the diluted aqueous solution has an alcohol content of about 12 to 21% by volume and a temperature of less than about 65° C.

8. The process of claim 6, wherein the diluted aqueous solution has a temperature of less than about 60° C. and a pH of about 1.5 to 2.5.

9. The process of claim 8, wherein the diluted aqueous solution has a temperature of about 35° to 55° C. and an alcohol content of about 12 to 21% by volume.

10. The process of claim 1, wherein the lignin-containing solution contains water before it is diluted with the water and acid.

11. The process of claim 10, wherein the lignin-containing solution is intimately and rapidly mixed with a mixture of the water and acid to form the diluted aqueous solution.

12. The process of claim 1, wherein the lignin-containing solution is obtained by: contacting wood or other fibrous plant material with the organic solvent at an elevated temperature and an elevated pressure to produce a cellulose pulp and a black liquor containing lignin and the organic solvent; and then separating the pulp from the black liquor.

13. The process of claim 12, wherein the acid and water are in a mixture which also contains hemicelluloses, other saccharides, extractives and lignin with a molecular weight of less than about 400 g/mol.

14. The process of claim 13, wherein the acid and water mixture is a recycled aqueous acid obtained by: diluting the black liquor with the aqueous acid to form a diluted black liquor from which lignin is precipitated, leaving a black liquor supernatant; removing the black liquor precipitate from the black liquor supernatant; removing the organic solvent from the black liquor supernatant to produce a residual black liquor supernatant; and then recycling a portion of the residual black liquor supernatant for use as the aqueous acid in diluting the black liquor.

15. The process of claim 14, wherein the organic solvent is a lower aliphatic alcohol of 1 to 4 carbon atoms.

16. The process of claim 15, wherein the diluted black liquor has a pH of less than about 2.5.

17. The process of claim 16, wherein the diluted black liquor has a temperature of less than about 60° C.

18. The process of claim 15, wherein the diluted black liquor has an alcohol content of about 10 to 25% by volume.

19. The process of claim 18, wherein the diluted black liquor has a pH of about 1.5 to 2.5 and a temperature of less than about 60° C.

20. The process of claim 19, wherein the diluted black liquor has a temperature of about 35° to 55° C. and an alcohol content of about 12 to 21% by volume.

21. The process of claim 14, wherein the black liquor contains water before it is diluted with the recycled aqueous acid.

22. The process of claim 21, wherein the black liquor is intimately and rapidly mixed with the recycled aqueous acid to form the diluted black liquor.

23. The process of claim 15, wherein the black liquor has a temperature of about 70° to 95° C. and the recycled aqueous acid has a temperature of less than about 50° C.

24. The process of claim 23, wherein the black liquor has a temperature of about 80° to 92° C. and the recycled aqueous acid has a temperature of about 25° to 40° C.

25. A lignin precipitated by the process of claim 1.

26. The lignin of claim 25 having: a number average molecular weight of about 800 to 1500 g/mol; and a polydispersity of less than about 4.

27. The lignin of claim 26 having: a number average molecular weight of about 900 to 1300 g/mol; and a polydispersity of no more than about 3.

28. The lignin of claim 27 having: a polydispersity of only about 1.5 to 2.7.

29. The lignin of claim 25 which is a paste, a wet cake or a powder.

30. A lignin precipitated by the process of claim 12.

31. The lignin of claim 30 having: a number average molecular weight of about 800 to 1500 g/mol; and a polydispersity of less than about 4.

32. The lignin of claim 31 having: a number of average molecular weight of about 900 to 1300 g/mol; and a polydispersity of no more than about 3.

33. The lignin of claim 32 having: a polydispersity of only about 1.5 to 2.7.

34. The lignin of claim 30 which is a paste, a wet cake or a powder.

35. A lignin precipitated by the process of claim 13.

36. The lignin of claim 35 having: a number average molecular weight of about 800 to 1500 g/mol; and a polydispersity of less than about 4.

37. The lignin of claim 36 having: a number average molecular weight of about 900 to 1300 g/mol; and a polydispersity of no more than about 3.

38. The lignin of claim 37 having: a polydispersity of only about 1.5 to 2.7.

39. The lignin of claim 35 which is a paste, a wet cake or a powder.

40. A lignin precipitated by the process of claim 14.

41. The lignin of claim 40 having: a number average molecular weight of about 800 to 1500 g/mol; and a polydispersity of less than about 4.

42. The lignin of claim 41 having: a number average molecular weight of about 900 to 1300 g/mol; and a polydispersity of no more than about 3.

43. The lignin of claim 42 having: a polydispersity of only about 1.5 to 2.7.

44. The lignin of claim 40 which is a paste, a wet cake or a powder.

45. A lignin having: a number average molecular weight of about 800 to 1500 g/mol; a polydispersity of less than about 4; and a methoxyl content approximately equal to that of native lignin.

46. The lignin of claim 45 having: a number average molecular weight of about 900 to 1300 g/mol.

47. The lignin of claim 46 having: a polydispersity of no more than about 3.

48. The lignin of claim 47 having: a polydispersity of only about 1.5 to 2.7.

49. The lignin of claim 45 having a glass transition temperature.

50. The lignin of claim 49, wherein the glass transition temperature is about 100° to 170° C.

51. The lignin of claim 50, wherein the glass transition temperature is about 130° to 150° C.

52. The lignin of claim 45 which is a paste, a wet cake or a powder.

53. A process for producing lignin from a black liquor comprising a solution of lignin, hemicellulose, and a water miscible organic solvent, comprising the steps of:
    precipitating lignin solids by diluting said black liquor with water and acid under conditions to form a diluted residual black liquor including a diluted residual black liquor supernatant and precipitated lignin solids which are free from the formation of tarry lignin precipitates;
    recovering said lignin by separating said lignin solids from said diluted residual black liquor supernatant.

54. A process as in claim 53 further including the step of flashing said black liquor to form a residual black liquor after recovery of a portion of said organic solvent under conditions which cool the residual black liquor without causing premature precipitation of said lignin;

55. A process, as in claim 54, wherein during said flashing step said residual black liquor is cooled to a temperature within the range of about from 70° C. to 95° C.

56. A process for producing lignin, as in claim 54, wherein said conditions include the formation of a diluted residual black liquor solution having a pH of less than about 3, an organic solvent content of less than about 30% by volume, and a temperature of less than about 75° C.

57. A process, as in claim 54, wherein said water and acid utilized in diluting said residual black liquor is an aqueous acid obtained by removing organic solvent from said diluted residual black liquor supernatant to produce a residual black liquor bottoms stream and recycling a portion of said residual black liquor bottoms stream for use as said aqueous acid.

58. A process, as in claim 57, wherein said residual black liquor bottoms stream is cooled to a temperature of less than about 50° C. prior to said recycling step and said cooled residual black liquor bottoms stream is used as said aqueous acid.

59. A process, as in claim 57, wherein recycling a portion of said residual black liquor bottoms stream comprises adding a water soluble acid to said residual black liquor bottoms stream to form an aqueous solution having a pH between approximately 1.0 and approximately 3.0.

60. A process for producing lignin comprising the steps of:
    containing wood or other fibrous plant material with an aqueous organic solvent to produce a cellulose pulp and a black liquor containing lignin and hemicellulose;
    separating said pulp from said black liquor;
    flashing said black liquor to form a residual black liquor with recovery of a portion of said organic solvent under conditions which cool the residual black liquor without causing premature precipitation of said lignin;
    diluting said residual black liquor with an aqueous acid to form a diluted residual black liquor supernatant and precipitated lignin solids, free from the formation of tarry lignin precipitates;
    recovering said lignin solids by separating said lignin solids from said diluted residual black liquor supernatant;
    removing said organic solvent from said diluted residual black liquor supernatant to produce residual black liquor bottoms stream;
    recycling a portion of said residual black liquor bottoms stream for use as said aqueous acid in diluting said residual black liquor whereby said residual black liquor is diluted with said aqueous acid under conditions to form a diluted residual black liquor supernatant and precipitated lignin solids, free from the formation of tarry lignin precipitates;
    recovering said lignin solids by separating said lignin solids from said diluted residual black liquor supernatant;

61. A process, as in claim 60, wherein during said dilution step, the ratio of residual black liquor to aqueous acid solution is in the range of from about 0.2 to 1.0.

* * * * *